(12) United States Patent
Kim (10) Patent No.: US 8,600,528 B2
(45) Date of Patent: Dec. 3, 2013

(54) REAL-TIME, PACKET-LEVEL QUALITY ASSURANCE OF ELECTROMECHANICAL DEVICE CONTROL DATA

(75) Inventor: Daniel Young-joon Kim, Cortland, NY (US)

(73) Assignee: The Research Foundation of State University of New York, Albany, NY (US)

( * ) Notice: Subject to any disclaimer, the term of this patent is extended or adjusted under 35 U.S.C. 154(b) by 566 days.

(21) Appl. No.: 11/857,017

(22) Filed: Sep. 18, 2007

(65) Prior Publication Data

US 2008/0069303 A1  Mar. 20, 2008

Related U.S. Application Data

(60) Provisional application No. 60/845,309, filed on Sep. 18, 2006.

(51) Int. Cl.
*G05B 9/00* (2006.01)
(52) U.S. Cl.
USPC .............................................. 700/79; 702/81
(58) Field of Classification Search
USPC .................. 700/79, 81; 378/65, 98, 98.2; 702/81–84, 108, 113, 182; 709/201, 709/203, 213, 219, 223, 224; 713/161; 707/1, 10, 100, 204; 606/1; 600/310
See application file for complete search history.

(56) References Cited

U.S. PATENT DOCUMENTS

| | | | |
|---|---|---|---|
| 4,064,459 A * | 12/1977 | Markwitz et al. | 375/228 |
| 5,081,678 A * | 1/1992 | Kaufman et al. | 713/161 |
| 6,173,325 B1 | 1/2001 | Kukreja | |
| 6,194,378 B1 | 2/2001 | Clark et al. | |
| 6,373,842 B1 | 4/2002 | Coverdale et al. | |
| 6,464,136 B2 * | 10/2002 | Walsh | 235/380 |
| 6,497,358 B1 * | 12/2002 | Walsh | 235/380 |
| 6,505,247 B1 * | 1/2003 | Steger et al. | 709/224 |
| 6,574,503 B2 * | 6/2003 | Ferek-Petric | 600/523 |
| 6,629,060 B2 * | 9/2003 | Okuno et al. | 702/187 |
| 6,637,649 B2 * | 10/2003 | Walsh | 235/380 |
| 6,643,818 B1 * | 11/2003 | Valk | 714/776 |
| 6,830,180 B2 * | 12/2004 | Walsh | 235/385 |
| 6,910,626 B2 * | 6/2005 | Walsh | 235/380 |
| 6,937,964 B2 * | 8/2005 | Okuno et al. | 702/187 |
| 7,027,437 B1 | 4/2006 | Merchant et al. | |
| 7,055,174 B1 | 5/2006 | Cope et al. | |
| 7,065,057 B2 | 6/2006 | Lucioni et al. | |
| 7,080,141 B1 | 7/2006 | Baekelmans et al. | |
| 7,142,512 B1 * | 11/2006 | Kobayashi et al. | 370/232 |

(Continued)

*Primary Examiner* — Charles Kasenge
(74) *Attorney, Agent, or Firm* — Scully, Scott, Murphy & Presser, P.C.

(57) ABSTRACT

The present invention relates to a method and system for providing real-time packet-level quality assurance of digital data that controls an electromechanical device transmitted through a network between a transmitting computer and at least one terminal computer. Specifically, all data packets transmitted between the transmitting computer and the at least one terminal computer are passively monitored, and those data packets containing digitized data that controls an electromechanical device of a pre-determined format are selectively recorded to a database. The selectively recorded data packets are then analyzed for determining whether a current set of digitized data that controls an electromechanical device transmitted between the transmitting computer and the at least one terminal computer during a current session would lead to a harmful or undesirable outcome by the electromechanical device being controlled. Finally, the analysis results are displayed in a real-time manner to provide real-time packet-level quality assurance of the digitized data that controls an electromechanical device.

21 Claims, 8 Drawing Sheets

(56) References Cited

U.S. PATENT DOCUMENTS

| | | | |
|---|---|---|---|
| 7,371,007 B2 * | 5/2008 | Nilsson | 378/207 |
| 7,415,639 B2 * | 8/2008 | Walz | 714/57 |
| 7,574,251 B2 * | 8/2009 | Lu et al. | 600/427 |
| 7,609,809 B2 * | 10/2009 | Kapatoes et al. | 378/65 |
| 7,639,854 B2 * | 12/2009 | Schnarr et al. | 382/128 |
| 7,643,661 B2 * | 1/2010 | Ruchala et al. | 382/128 |
| 7,773,788 B2 * | 8/2010 | Lu et al. | 382/128 |
| 2001/0004352 A1 * | 6/2001 | Watanabe et al. | 370/252 |
| 2005/0283684 A1 * | 12/2005 | Walz | 714/47 |
| 2006/0160498 A1 * | 7/2006 | Sudo | 455/103 |
| 2006/0285639 A1 * | 12/2006 | Olivera et al. | 378/65 |
| 2006/0285640 A1 * | 12/2006 | Nizin et al. | 378/65 |
| 2007/0041494 A1 * | 2/2007 | Ruchala et al. | 378/65 |
| 2007/0041497 A1 * | 2/2007 | Schnarr et al. | 378/65 |
| 2007/0041499 A1 * | 2/2007 | Lu et al. | 378/65 |
| 2007/0115918 A1 * | 5/2007 | Bodin et al. | 370/352 |
| 2007/0186180 A1 * | 8/2007 | Morgan | 715/779 |
| 2007/0201613 A1 * | 8/2007 | Lu et al. | 378/65 |
| 2009/0109858 A1 * | 4/2009 | Yamasaki et al. | 370/242 |

* cited by examiner

REAL-TIME, PACKET-LEVEL QUALITY ASSURANCE OF ELECTROMECHANICAL DEVICE CONTROL DATA

CROSS REFERENCE TO RELATED APPLICATION

The present application claims benefit of U.S. Provisional Application No. 60/845,309 filed on Sep. 18, 2006.

FIELD OF THE INVENTION

The present invention relates to systems and methods for providing packet-level quality assurance of digital data that control an electromechanical device such as medical linear accelerators, automated prescription-filling systems, and stereotactic radiosurgery devices, which are transmitted through a packet-switched network between a transmitting computer and at least one terminal computer. More specifically, the present invention relates to systems and methods for providing packet-level quality assurance of radiation treatment data, such as multi-leaf collimator (MLC) position data, that are transmitted through a network between a transmitting computer, which stores medical and clinical information used by a medical institute, and at least one terminal computer, which controls the operation and output of radiation treatment equipment according to the data provided by the transmitting computer.

BACKGROUND OF THE INVENTION

Delivery of linear accelerator-generated radiation therapy to cancer patients is typically controlled by a complex network of personal computers (PCs). Specifically, the radiation treatment data, such as the quantity of radiation to deliver and the geometrical configuration of beam-blocking materials (e.g., multi-leaf collimators or MLC) that shape the radiation beam to match the shape of the malignancy within the patient, are typically generated by physicians on a treatment-planning computer (not shown) and are then downloaded into a central database server that is connected with the treatment-planning computer. The central database server also stores other medical and clinical information that are used by a medical institute. The radiation treatment data and other medical and clinical data are then transmitted from the central database server through a network to multiple terminal computers, i.e., terminals 1, 2, and 3, . . . , each of which controls the operation of a set of radiation equipment in a remote treatment room for actual delivery of the radiotherapy, as shown in FIG. 1.

Because radiation treatment data for a particular patient must remain secure throughout the course of treatment, which typically runs for weeks, there is a potential risk that the radiotherapy data stored in the central database server may become corrupted subsequent to the initial verification and approval of such data. Furthermore, although low-level network protocols contain safeguards against the miscommunication of data, the possibility nevertheless exists that radiation treatment data may be incorrectly transmitted between any of the data transmission links between the central database server and the individual terminal computers.

Execution of such miscommunicated or corrupted radiation treatment data by the radiation treatment equipment can lead to patient harm and potential medical malpractice liability. In April 2005, the Federal Drug Administration (FDA) reported an incident in which the miscommunication of radiation treatment data between two computers led to the over-treatment of a head and neck cancer patient by 3 to 4 times the intended radiation dose. Reference: FDA Adverse Event Report No. 2914292-2005-00003; New York State Department of Health, Notices No. BERP 2005-1 and BERP 2005-2.

Figure 1:
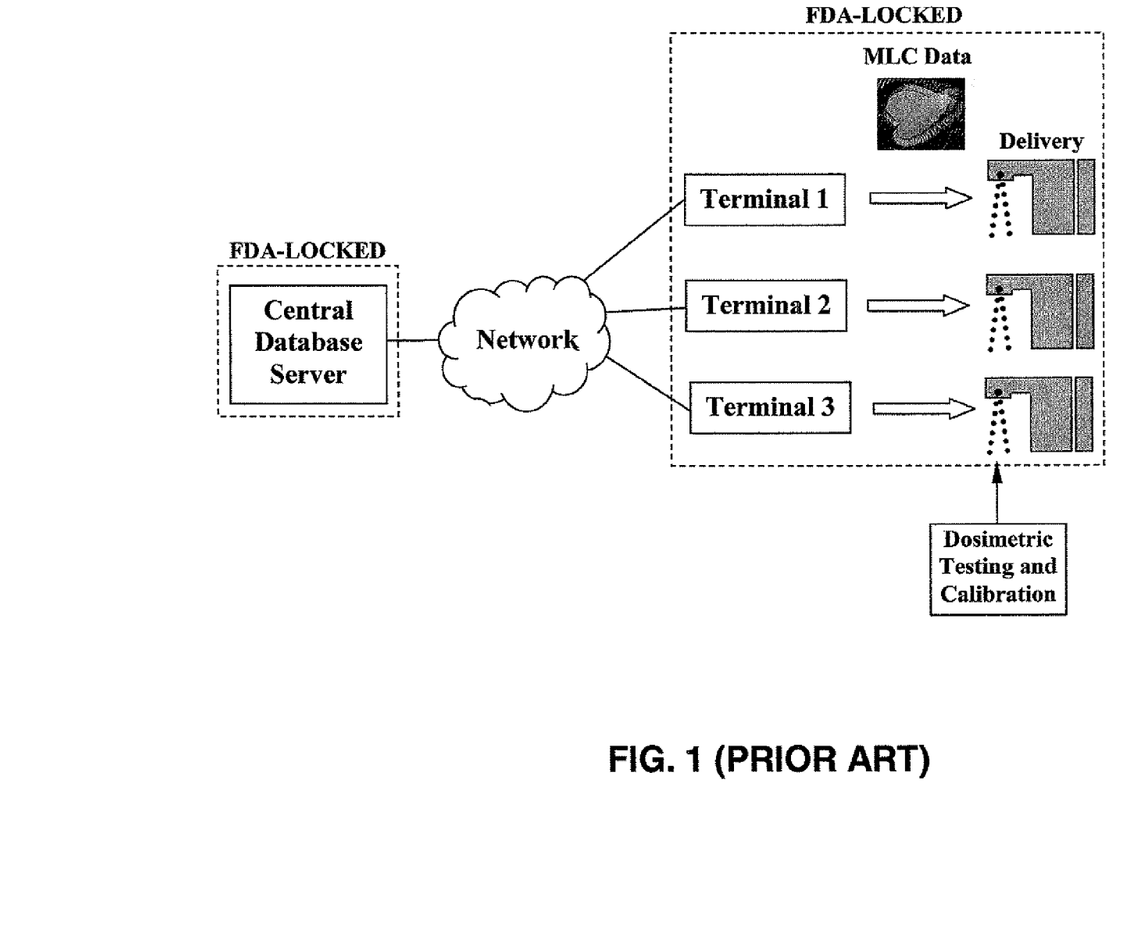
FIG. 1 is a schematic representation of a conventional network for connecting a transmitting computer, e.g. a central database server and multiple terminal computers that control operation of radiation treatment equipment for delivery of radiation treatment data.

Conventional radiation treatment quality assurance (QA) systems or methods employ actual measurement and calibration of the radiation beams generated by the radiation treatment equipment, as shown in FIG. 1. The dosimetric testing and calibration ensure that the radiation treatment equipment accurately delivers the specified amounts of radiation at the specified locations, according to the radiation treatment data furnished by the terminal computers. Typically, a dosimetric verification measurement of specific patient delivery plans is performed a few days before the commencement of that patient's course of treatment. However, because this measurement is time consuming, it is usually done only once. Unfortunately, such conventional dosimetric approaches cannot prevent the apparently "correct" execution of miscommunicated or corrupted radiation treatment data by the equipment at the actual time of treatment, which can lead to severe radiation over-doses.

Therefore, a need exists for a method and system for providing real-time verification of the radiation treatment data and real-time detection of data error caused by either miscommunication or corruption during storage, immediately before each actual delivery of radiation treatment to the patients.

In addition, the FDA characterizes the central database server and the terminal control computers as parts of the radiation treatment system and prohibits users from tampering or otherwise modifying them.

Accordingly, there is a further need for a method and system that can successfully carry out data verification and data error detection functions without modifying any portion of the FDA-approved radiation treatment system, including the transmitting computer and the terminal control computers.

SUMMARY OF THE INVENTION

The present invention provides a method and system for passively monitoring data traffic over a network between a transmitting computer and at least one terminal computer, selectively recording target data, e.g. digitized data that controls an electromechanical device of a predetermined format, to a database, analyzing the selectively recorded digitized data that controls an electromechanical device to detect potential data errors caused by miscommunication or corruption during storage, and providing real-time output of the potential data errors, e.g. on a display intended to be seen by human operators.

The method and system of the present invention are particularly useful for verifying and detecting errors in the radiation treatment data, such as MLC configuration data and/or associated field data for a particular patient. However, the method and system of the present invention can also be used for verifying and detecting errors in the control data of any other types of electromechanical devices, in which the control data are transmitted between any two computers on a packet-switched network. Contemplated "electromechanical devices" include but are not limited to: medical linear accelerators, automated prescription-filling systems, stereotactic radiosurgery devices, CT scanning devices, X-ray devices, non-medical robotic devices, timers, and the like.

In one aspect, the present invention relates to a method for providing real-time packet-level quality assurance of target data, e.g. digitized data that controls an electromechanical device, that are transmitted through a network between a transmitting computer, e.g. a central database server and at least one terminal computer, comprising:

passively monitoring all data packets transmitted through the network between the transmitting computer and the at least one terminal computer;

selectively recording data packets that contain digitized data that controls an electromechanical device of a pre-determined format to a database;

analyzing the data packets stored in the database to determine whether a current set of target data transmitted through the network between the transmitting computer and the at least one terminal computer during a current session are control data that would lead to a harmful or undesirable outcome by the electromechanical device being controlled; and providing real-time output and display of analysis results.

Preferably, but not necessarily, the transmitting computer is a central medical database server that stores all medical and clinical information used by a medical institute; the at least one terminal computer controls operation of radiation treatment equipment at a remote location; and the target data are radiation treatment data. More preferably, the target data comprises multi-leaf collimator (MLC) data for either static radiation treatment or intensity modulated radiation therapy (IMRT), or the target data comprises the quantity of radiation to be generated by the linear accelerator (Monitor Units or MUs); or the target data comprises the identifying information, such as the name, of the patient to be treated.

A data quality assurance device is preferably provided for passively monitoring, selectively recording, analyzing data packets transmitted through the network between the transmitting computer and the at least one terminal computer, and providing real-time output and display of the analysis results. In one aspect, the real-time output of analysis results can be communicated to a secondary, tertiary or other peripheral or remote computer system.

The network is preferably a switched network comprising a switch that simultaneously connects the transmitting computer with multiple terminal computers, including said at least one terminal computer.

In one specific embodiment of the present invention, the switch is arranged and constructed to mirror all data traffic between the transmitting computer and the multiple terminal computers to the data quality assurance device.

In an alternative embodiment of the present invention, at least one packet-copying device is arranged and constructed to copy all data packets transmitted between the transmitting computer and other terminal computers to the data quality assurance device. Further, additional packet-copying devices can be provided to copy all data packets transmitted between the central database server and other terminal computers to the data quality assurance device. Packet-copying devices that are suitable for practicing the present invention include, but are not limited to: hubs, network taps, etc.

In another aspect, the present invention relates to a system comprising:

a transmitting computer;

at least one terminal computer connected to the transmitting computer by a network, wherein data packets are transmitted between the transmitting computer and the terminal computer through the network; and a data quality assurance device connected to the network, wherein the data quality assurance device is arranged and constructed for: (1) passively monitoring all data packets transmitted between the transmitting computer and the at least one terminal computer; (2) selectively recording data packets that contain digitized data that controls an electromechanical device of a pre-determined format to a database; (3) analyzing the data packets stored in the database to determine whether a current set of digitized data that controls an electromechanical device transmitted between the central database server and the at least one terminal computer during a current session are control data that would lead to a harmful or undesirable outcome by the electromechanical device being controlled, and (4) providing real-time output and display of analysis results.

Other aspects, features and advantages of the invention will be more fully apparent from the ensuing disclosure and appended claims.

BRIEF DESCRIPTION OF THE DRAWINGS

The accompanying drawings, which are incorporated in and form a part of this specification, illustrate embodiments of the invention and, together with the description, serve to explain the principles of the invention.

The drawings referred to in this description are not to scale, expect when specifically noted.

DETAILED DESCRIPTION OF THE INVENTION, AND PREFERRED EMBODIMENTS THEREOF

Reference will now be made in detail to the preferred embodiments of the invention, examples of which are illustrated in the accompanying drawings. While the invention will be described in conjunction with the preferred embodiments, it will be understood that they are not intended to limit the invention to these embodiments. On the contrary, the invention is intended to cover alternatives, modifications, and equivalents, which may be included within the spirit and scope of the invention as defined by the appended claims. Furthermore, in the following detailed description of the present invention, numerous specific details are set forth in order to provide a thorough understanding of the present invention. However, one ordinarily skilled in the art can readily appreciate that the present invention may be practiced without these specified details. In other instances, well-known methods, procedures, components and circuits have not been described in detail as not to unnecessarily obscure aspects of the present invention.

Some portions of the detailed descriptions, as illustrated hereinafter, are present in terms of procedures, logic blocks, processing, and other symbolic representations of operations on data bits within a computer memory. These descriptions and representations are means used by those ordinarily skilled in the data processing art to most effectively convey the substance of their work to others skilled in the art. For example, a procedure, logic block, process, etc., is conceived to be a self-consistent sequence of steps or instructions leading to a desired result.

The steps are those requiring physical manipulations of physical quantities. Usually, though not necessarily, these quantities take the form of electrical or magnetic signals capable of being stored, transferred, combined, compared, and otherwise manipulated in a computer system. It has proved convenient at times, principally for reasons of common usage to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the following discussions, it is appreciated that throughout the present invention, discussions utilizing terms such as "storing," "downloading," "prompting," "running" or the like, refer to the actions and processes of a computer system, or similar electronic computing device. The computer system or similar electronic computing device manipulates and transforms data represented as physical (electronic) quantities within the computer system's registers and memories into other data similarly represented as physical quantities within the computer system memories or registers or other such information storage, transmission, or display devices. The present invention is also well suited to the use of other computer systems such as, for example, optical and mechanical computers. The terms "digital" and "digitized" are used synonymously herein.

The term "real-time" as used herein refers to performance of a computer system that receives and processes data quickly enough to produce output to control, direct or affect the outcome of an ongoing activity or process. For example, the computations necessary to verify the radiation treatment data are performed quickly enough, so that any potential data error caused by miscommunication or corruption can be detected and reported to the operator prior to the actual delivery of the radiation treatment.

The term "transmitting computer" as used herein refers to a commonly understood computing device that originates data packets sent over a computer network which targets a receiving computer. An example of a "transmitting computer" as contemplated by the present invention is a central database server "Transmitting computers" as used herein also refers to intermediary control computers, i.e. computers whose functions include the (re-)transmission of control data received by the central database server, to the electromechanical device(s) ultimately controlled by the transmitted data; as well as computers that manipulate data that will eventually effect the treatment delivery, such as workstations used by individual doctors, technicians and hospital, clinical or appropriately trained office staff, treatment-planning computers, simulation computers, and image servers.

The present invention provides an innovative system and method for per-fraction, pre-treatment, and vendor-independent verification of MLC configuration data and radiation quantity (Monitor Unit) data.

The hardware required for practicing the present invention is relatively simple. Specifically, FIG. 2 shows a system comprising a central database server that is connected through a network to multiple terminal computers 1, 2, 3, . . . , etc., each of which controls a set of radiation treatment equipment at a remote location from the central database server, as shown in FIG. 2.

Figure 2:
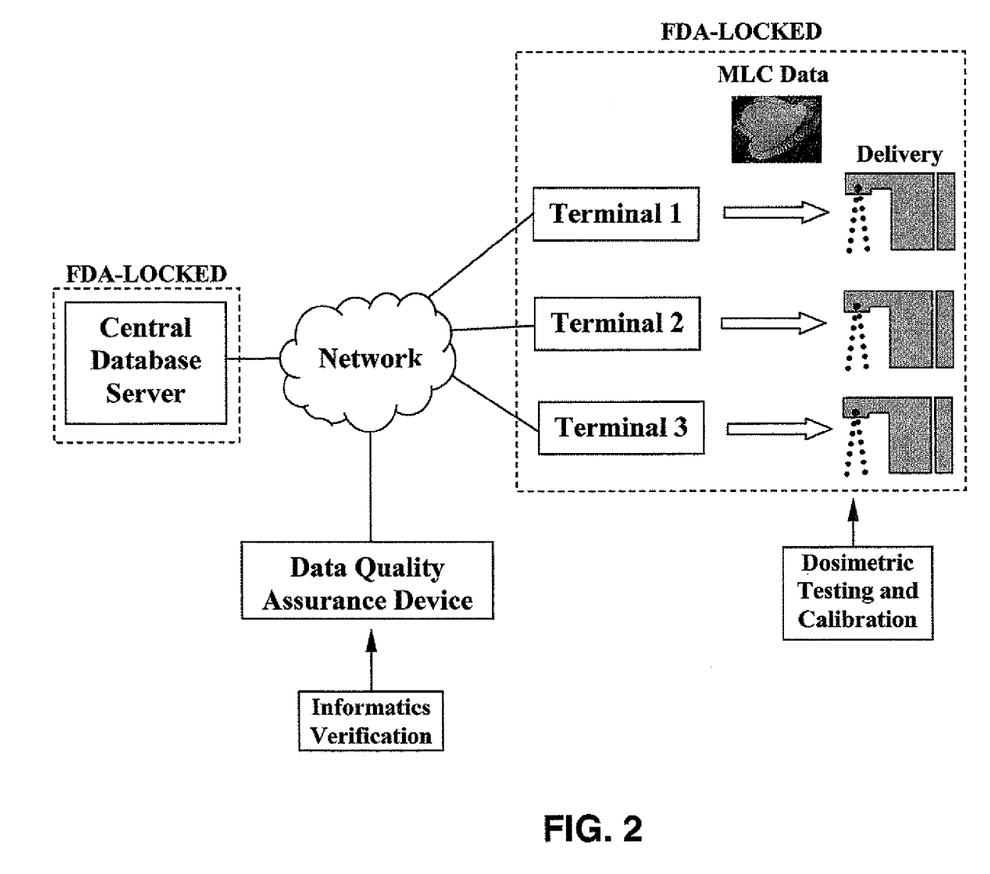
FIG. 2 is a schematic representation of an exemplary data quality assurance device connected to a network between a transmitting computer, e.g. a central database server and multiple terminal computers for informatics-based verification of the radiation treatment data transmitted from the central database server to the multiple terminal computers, according to one embodiment of the present invention.

Note that FIG. 2 is only a schematic representation of an exemplary system according to one embodiment of the present invention, and it should not be construed in any manner as limiting the broad scope of the present invention. For example, the system of the present invention may comprise any suitable number of terminal computers from 1 to several hundreds. At least one of such terminal computers is connected with a set of radiation treatment equipment for controlling thereof, and the other terminal computers can be connected with either radiation treatment equipment, or other medical equipment for diagnosis, monitoring, and treatment of patients. The system of the present invention may comprise other computers and devices besides the central database server and the terminal computers. Such other computers and devices include, for example, workstations used by individual doctors and staff, treatment-planning computers, image servers, simulation computers, routers, etc. The detailed configuration of computer networks for medical institutes is well known in the art and is therefore not described herein to avoid obscuring the present invention.

The central database server and the terminal computers can comprise any number of suitable general-purpose computers, specific-purpose computers, workstations, lap-tops, etc. Each computer comprises computer readable media such as, for example, a hard drive, a floppy disk, an optical disc, a magnetic tape, a compact disc, and the like coupled thereto for running of one or more suitable software. In a particularly preferred, but not necessary, embodiment of the present invention, the central database server runs Varis 7 clinical informatics software, which performs the administrative data management tasks and controls the treatment delivery process, the recordation, and the verification processes. The terminal computers are preferably control computers for Varian 21EX (120-leaf dynamic MLC) and/or Varian 2100-2 (52-leaf static MLC) radiation treatment equipment. However, any art recognized appropriate radiation treatment equipment is suitable for use in accordance with the present invention.

Any suitable network can be used for connecting the computers in the present invention, including, but not limited to local area networks (LAN), such as Ethernet, token ring, FDDI, and ARCNET, and wide area networks (WAN), such as WiFi. The network may include any suitable networking elements, which are not shown in FIG. 2 but are contemplated by the present invention. In a particularly preferred, but not necessary, embodiment of the present invention, the computers are connected by Ethernet.

A data quality assurance device is connected to the network for passively monitoring, selectively recording, and analyzing data packets that contain radiation treatment data and are transmitted between the central database server and the terminal computers, as shown in FIG. 2. The data quality assurance device is configured to perform its functions without in any manner interfering with the data traffic between the central database server and the terminal computers. In other words, the data quality assurance device is considered absolutely "passive" to the central database server and the terminal computers. Therefore, the data quality assurance device of the present invention is vendor-independent and should not invalidate FDA approval of the computer systems under observation.

The data quality assurance device may comprise any suitable general-purpose computer, specific-purpose computer, workstation, lap-top, etc. The data quality assurance device further comprises computer readable media such as, for example, a hard drive, a floppy disk, an optical disc, a magnetic tape, a compact disc, and the like coupled thereto for running of one or more suitable software. In a particularly preferred, but not necessary, embodiment of the present invention, the data quality assurance device is a typical Pentium 4 workstation (Dell Optiplex GX 260) that is equipped with two network interface cards and runs the i586 compilation of Mandriva Linux 2006 operating system. Various software packages, such as Pcap, Snort, Barnyard, mySQL, PHP, Apache, etc., can be installed on the data quality assurance device, and the functions and equivalents of such exemplary software packages will be described in greater detail hereinafter.

Figure 3:
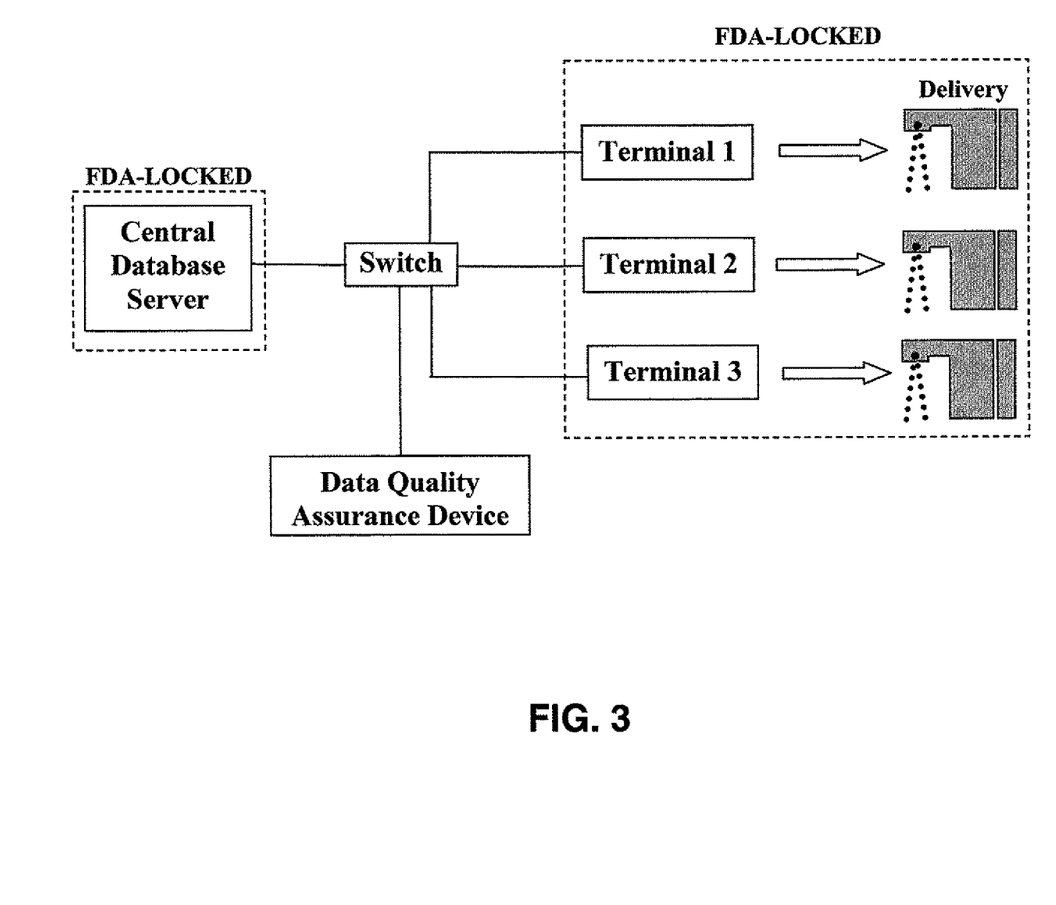
FIG. 3 is a schematic representation of an exemplary switched network comprising a switch that simultaneously connects a transmitting computer e.g. a central database server with multiple terminal computers, while the switch is arranged and constructed to mirror all data traffic between the central database server and the multiple terminal computers to a data quality assurance device, according to one embodiment of the present invention.
Figure 4:
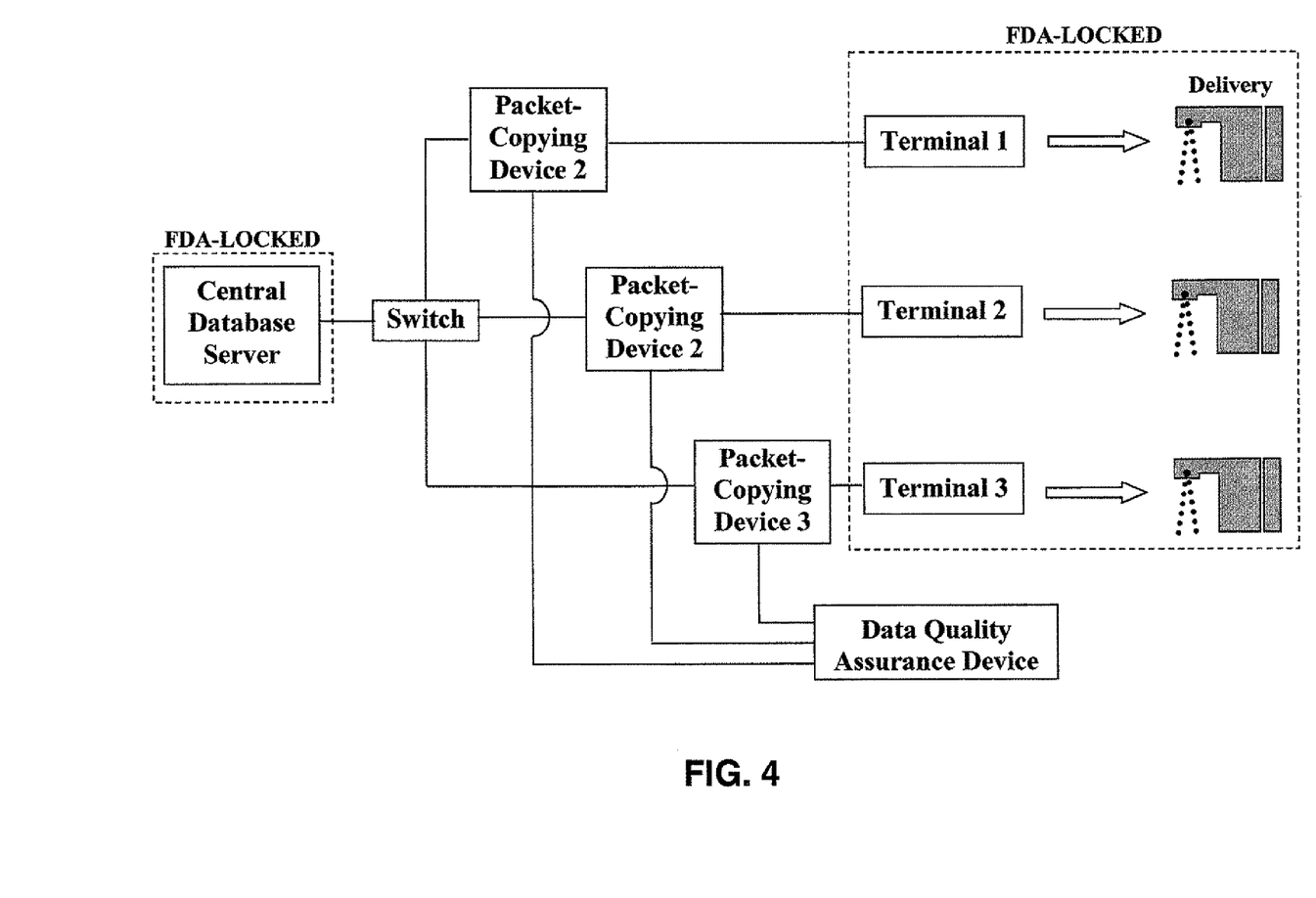
FIG. 4 is a schematic representation of an exemplary switched network comprising a switch that simultaneously connects a transmitting computer e.g. a central database server with multiple terminal computers and multiple packet-copying devices arranged and constructed to copy all data traffic between the central database server and the multiple terminal computers to a data quality assurance device, according to one embodiment of the present invention.

The data quality assurance device of the present invention can be connected to the network by various means, depending on the specific configuration of the network. When the network is a switched network (such as Ethernet) that comprises a switch for simultaneously connecting the central database server with the multiple terminal computers, the data quality assurance device can be connected directly to the switch, which is then arranged and constructed for mirroring all the data traffic between the central database server and all the terminal computers to the data quality assurance device, as shown in FIG. 3. Alternatively, the data quality assurance device can be connected to multiple packet-copying devices, each of which is provided on a data transmission path between the central database server and an individual terminal computer, so that all data traffic between the central database server and the terminal computers are copied to the data quality assurance device, as shown in FIG. 4. It is also possible to provide one or more packet-copying devices on one or more specific data transmission paths between the central database server and one or more individual terminal computers to copy the data packets sent by the central database server to such one or more individual terminal computers.

Figure 5:
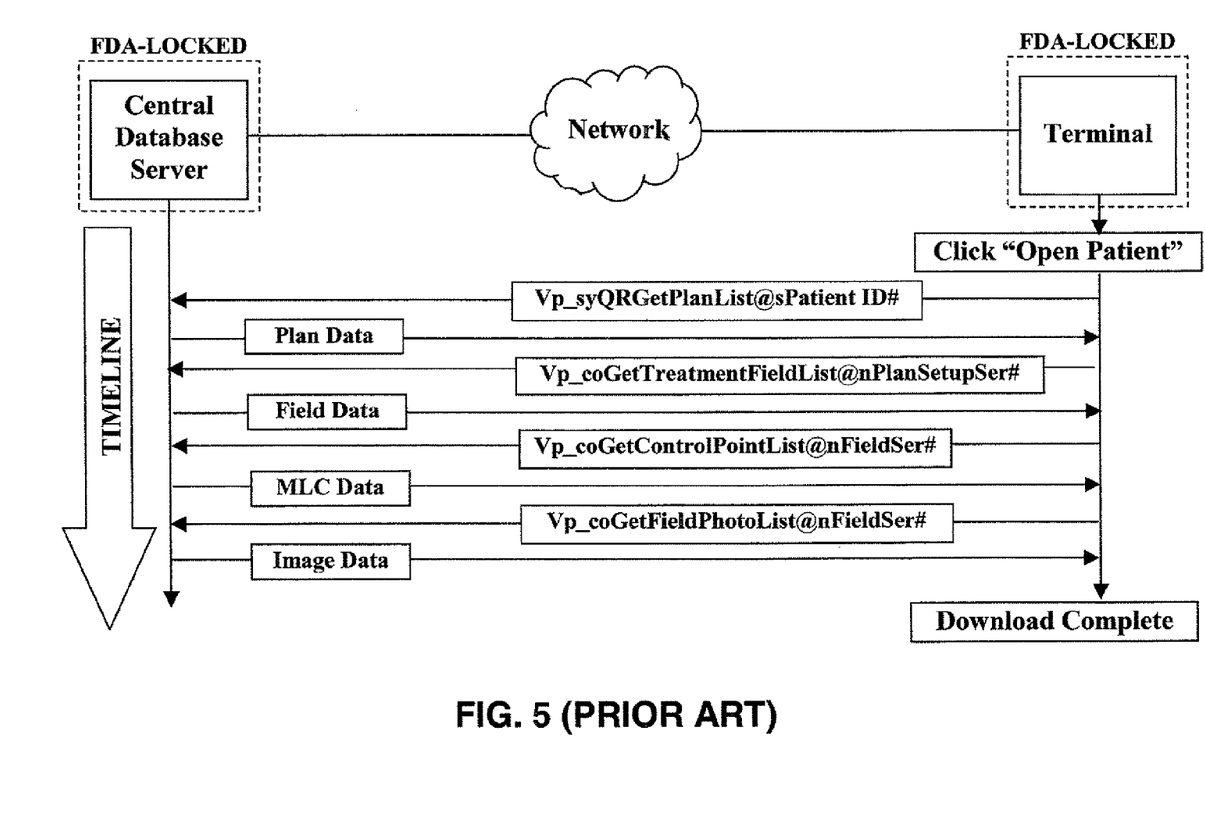
FIG. 5 shows a timeline of the conventional sequence of packet data transmission between the transmitting computer, e.g. central database server and a specific terminal computer, which occurs when the medical accelerator operator "opens" a patient treatment plan file for imminent treatment delivery, at the control console.

When a particular patient file is selected and opened by the operator for a current radiation treatment session, clinical data for the entire treatment session is sent from the central database server to the terminal computer in the form of several thousands of packets. The data transfer from the central database server to the terminal computer is initiated by request packets sent from the terminal computer to the central database server. The information embedded in each request packet describes the type of data being requested, and the sequence of data request and transfer between the central database server and the terminal computer before initiation of a specific radiation treatment session is shown in FIG. 5. For example, in response to a request packet containing the string "vp_syQRGetPlanList@sPatientID#," which identifies the specific patient on whom the current treatment session will be performed, the central database server will send the plan data for this specific patient. For another example, in response to a request packet containing the string "vp_coGetControlPointList@nFieldSer#," which identifies a specific field in the plan, the central database server will send the MLC configurations for the identified field. All the data sent by the central database server to the terminal computer are transmitted in form of a series of data fragments (i.e., packets), which must be processed by the terminal computer in order to reconstruct the desired data. Once all the clinical data related to the current treatment session has been downloaded onto the terminal computer, patient-related network traffic between the terminal computer and the central database server then ceases during the treatment session. When the treatment is complete, the verification data is written by the terminal computer and sent back to the central database server in the form of a few thousand packets.

Since the MLC-related data packets only make up about 4% of the total clinical data transmission between the central database server and the terminal computer, it is important for the data quality assurance device of the present invention to be able to recognize the MLC data (or other types of target data) and distinguish the MLC data packets from various data packets that are also transmitted between the central database server and the terminal computer but are irrelevant to the intended analysis or verification. By "target data" as used herein is meant digitized data that controls an electromechanical device.

Therefore, the data quality assurance device is equipped with: (1) art-recognized software for capturing all data packets transmitted over the network between the central database server and the terminal computer, and (2) a network data analyzer with a graphic interface for deducing the target data (such as the MLC data) during a deduction mode of operation.

Typically, data representing the specific leaf position of a single MLC leaf is 3 bytes in the form of 02yyxx, where 02 is a marker byte, and the leaf position (in thousandths of a centimeter at isocenter) is given by the hexadecimal-encoded number yyxx. The centerline, which is formed by the leaf tips when all MLC leaves are closed and centered, is defined as zero. Leaf overtravel is denoted by a negative number encoded in 2's complement.

A static 120-leafMLC configuration is transmitted in 360 bytes as a contiguous block of the 3-byte single-leaf positions described hereinabove. In other words, the static 120-leaf MLC data block contains contiguous 120 units of 02yyxx arranged in series (i.e., 02yyxx02yyxx02yyxx . . . ). The marker byte 02 therefore appears 120 times in a static 120-leaf MLC data block, and each marker byte 02 is equally spaced from the adjacent marker bytes, which constitutes a distinctive static MLC "signature" that can be used for searching potential static MLC data blocks whose positions within a larger data block are unknown.

The data representing a dynamic MLC or IMRT field is specified as a series of stack MLC configurations, typically numbering between 80 and 140. Each stack MLC data block is prefaced by an 89-byte-long header and followed by a 45-byte-long footer. The header includes a number related to how much radiation (i.e., radiation intensity) should be delivered to the patient in the given static MLC position.

The types of field (i.e., open, static MLC, or IMRT) can be readily determined from the number of packets sent by the central database server to the terminal computer in response to a "vp_coGetControlPointList" data request packet. Typically, 7 data packets are sent by the central database server for an open field; 8 data packets are sent for a static MLC field; and about 100 data packets are sent for an IMRT field.

The unique MLC signatures and field information, as deduced by a network analyzer and described hereinabove, can then be used for identifying, selectively recording, and analyzing the MLC data packets by the data quality assurance device of the present invention during an archive and analysis mode.

Figure 6A:
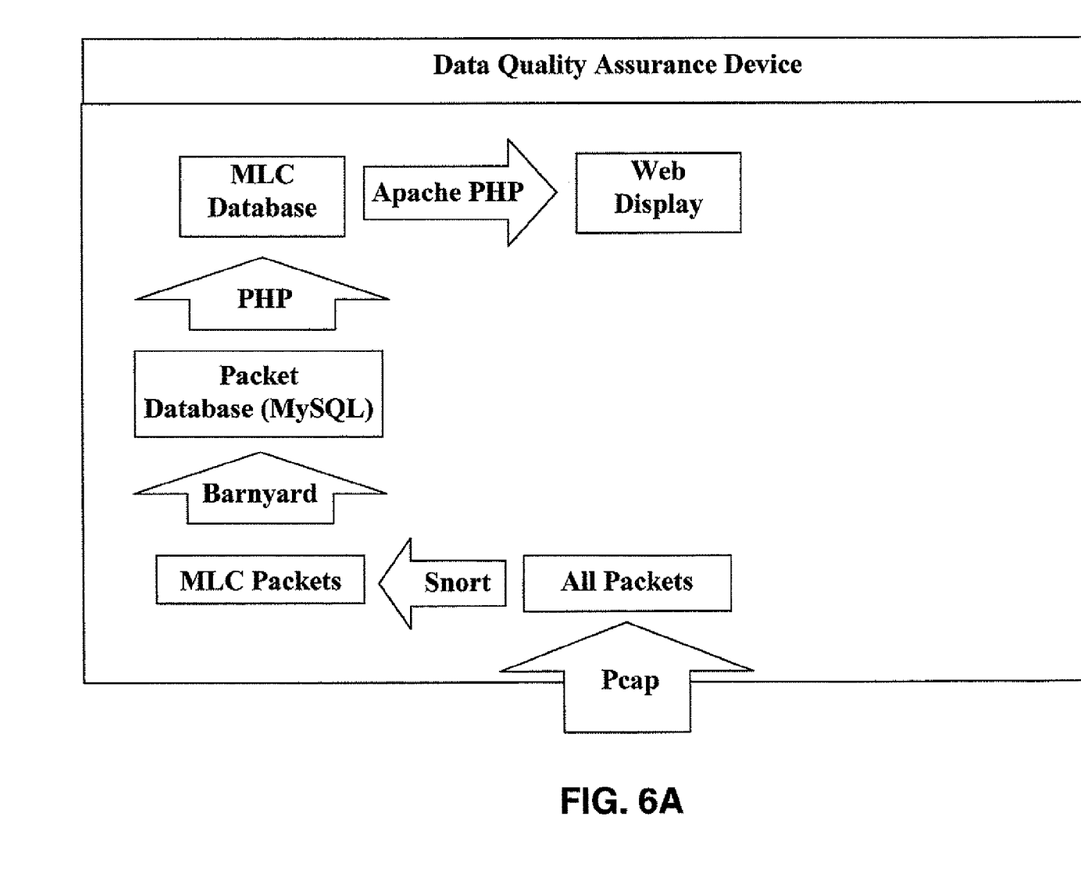
FIG. 6A shows an exemplary radiotherapy data quality assurance device that employs the Snort, Barnyard, MySQL, PHP, and Apache PHP software for real-time archiving and analyzing the MLC, MU, and patient identification configuration data, according to one embodiment of the present invention.

FIG. 6A shows an exemplary data quality assurance device that employs the Snort, Barnyard, MySQL, PHP, and Apache PHP software for real-time archiving and analyzing the MLC configuration data, according to one embodiment of the present invention. It is important to note that although the descriptions hereinafter are focused on specific software packages for illustration purposes, other software packages performing similar functions can be readily used in place of the specifically illustrated software packages for the purpose of practicing the present invention.

Specifically, the Snort network intrusion detection software package is installed on the data quality assurance device for selective recording of the MLC data packets and the related field information, and a custom Snort configuration file with the unique MLC packet signatures is written to provide Snort with the criteria to either commence or cease packet recording. The TCP stream reassembly feature of Snort allows reconstruction of conversational "streams" between computers from packets and is therefore particularly useful for the present invention. Snort also contains database output feature and can directly write the selectively recorded MLC data packets and related field information into a packet database moments after a new patient file is downloaded into the terminal computer. Alternatively, the Barnyard software package, which is an output spool reader for Snort, can be used in conjunction with Snort (as shown in FIG. 6A) to perform event processing from Snort's "unified file format." When Snort is configured for unified logging, the Snort engine can become more efficient by focusing only on packet analyzing and recording. In other words, Snort no longer needs to use resources on the output plug-ins to inject the event data into the packet database, and Barnyard now takes over that responsibility.

Although being in a database makes the captured packets easier to manipulate, such data packets are written into the database in binary form. It is therefore necessary to translate the binary data into human-readable physical quantities, such as MLC leaf positions. Correspondingly, a custom PHP script is written for reading the data from the binary packet database, parsing the binary code and translating useful data into human-readable format, and writing it into another human-readable database, such as the MLC database in FIG. 6A. The packets database as described hereinabove is preferably supported by the mySQL database server, as shown in FIG. 6A. PHP is a popular programming language that features easy access to database objects and seamless integration into web documents, and it is typically used in conjunction with the mySQL database server for database applications.

The final MLC database is an automatically updated, real-time database that archives all of the selectively recorded MLC data downloaded by the terminal computer from the central database server. It therefore provides a historical record of MLC configurations from all previous treatment sessions, accessible by the patient's ID number. For a given patient and field, the MLC data for different treatment sessions are normally identical. Therefore, any difference in the MLC data between the current session and a previous session signifies either corruption/miscommunication of the MLC data, or modification of the MLC data by a clinician. The data quality assurance device of the present invention, by comparing the MLC data for a current session and those for a previous session, can detect any difference therebetween and provide real-time output of the detection results. Apache, a web server, is then employed by the data quality assurance device of the present invention to provide web display of the detection results and allows web-based verification of patients' MLC data by any web browser in the clinical network of the medical institute.

Figure 6B:
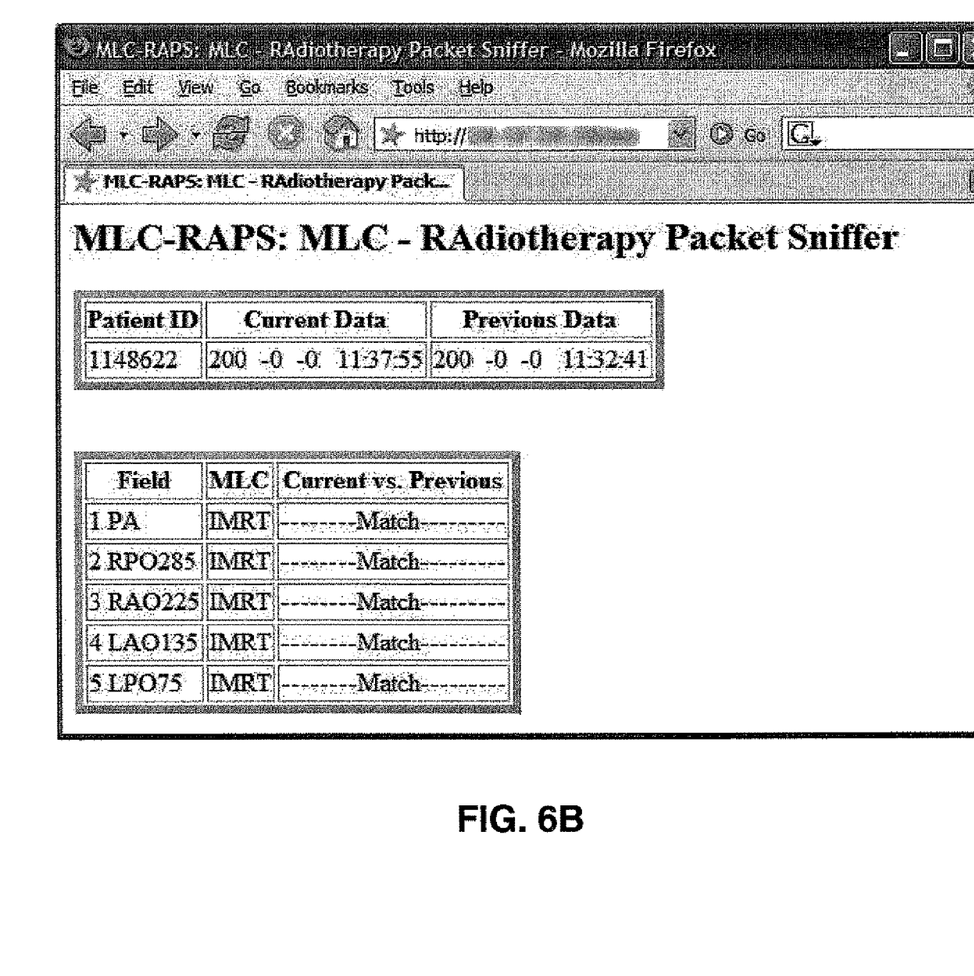
FIG. 6B shows an exemplary screenshot of a web-page display of the analytical results, as outputted by the radiotherapy data quality assurance device of FIG. 6A.

FIG. 6B shows an exemplary screenshot of a web-page display of the results of comparison between the MLC data for a current treatment session and those for a previous treatment session, as outputted by the data quality assurance device of FIG. 6A.

Figure 7:
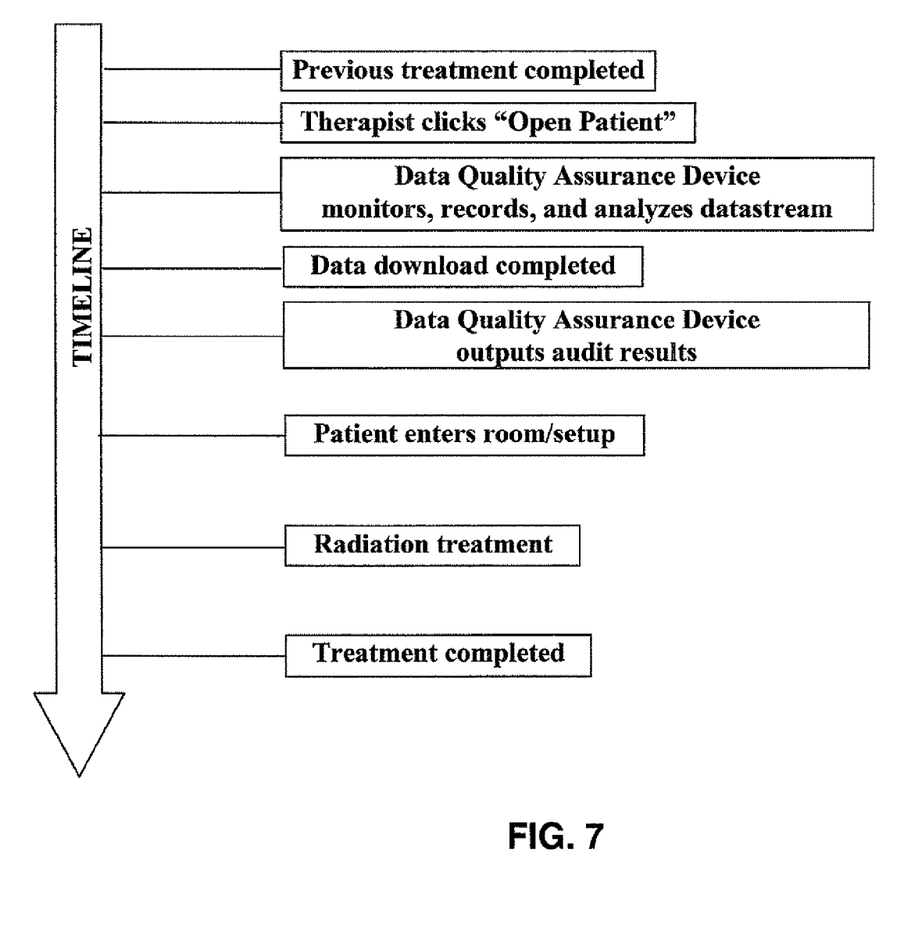
FIG. 7 shows a timeline of the sequence of events occurred during a radiation treatment session, while a radiotherapy data quality assurance device is provided for real-time archiving and verifying the MLC, MU, and patient identification configuration data prior to the actual delivery of the radiation treatment, according to one embodiment of the present invention.

More importantly, the data quality assurance device of the present invention can complete all the above-described tasks immediately after the MLC data download from the central database server onto the terminal computer and about 10-15 minutes before the patient receives their radiation treatment, as shown by the timeline of the sequence of events occurred during a radiation treatment session in FIG. 7. In this manner, the data quality assurance device of the present invention provides real-time verification of the MLC configuration data prior to actual delivery of the radiation treatment. If the MLC data for the current session match those for a previous session, the therapists or clinicians can safely perform the radiation treatment without having to worry about the possibility of MLC data miscommunication or corruption. If a mismatch is found between the MLC data for the current session and those for a previous session, a red flag is raised, which calls for a brief "time-out" before the actual treatment, during which the therapists or clinicians can conduct further verification of the MLC data.

The system and method of the present invention therefore provide a real-time, packet-level quality assurance for the radiation treatment data. More importantly, the system and method of the present invention examines and exploits the space (i.e., the network) between the FDA-locked equipment (i.e., the central database server and the terminal computers) to provide a vendor-independent, informatics-based quality assurance mechanism. This informatics-centered approach to MLC data quality assurance mechanism contrasts with, and also complements, the conventional measurement-based quality assurance techniques that focus on dosimetric verification of the MLC sequences. Both approaches can be used in conjunction to minimize the risk of radiation misadministration in medical institutes.

It is important to note that while FIGS. 2-7 illustratively demonstrate exemplary hardware and software configurations, according to specific embodiments of the present invention, it is clear that a person ordinarily skilled in the art can readily modify such configurations for adaptation to specific application requirements, consistent with the above descriptions. Further, while FIGS. 2-7 primarily refer to archiving and auditing of MLC or radiation treatment data, it should be appreciated that other types of data, which are transmitted between two computers in a repetitive manner with little or no variation from session to session, can also be archived and audited by the system and method of the present invention.

For example, the number of Monitor Units (MU) for a given radiation field, which is directly proportional to the quantity of radiation generated by the accelerator, is a crucial piece of electromechanical device control data that is a part of the "Field Data" shown in FIG. 5. The data quality assurance device depicted in FIG. 6A can display an alert, as in FIG. 6B, if the number of Monitor Units was an abnormally high (or low) number not normally used in clinical radiotherapy treatment, for example, less than 10 or greater than 500. Thus, in accordance with the present invention, data packets stored in the database can be objectively analyzed to assess and display, in real-time, whether a harmful or undesirable outcome is occurring or possible, causing an alert for the practitioner (e.g. physician, technician) who can then decline to commence the treatment (or abort the treatment if already started), in order to re-check the treatment parameter data and re-download the verified data to the electromechanical device being controlled.

In another example of a configuration adaptation which leads to an embodiment of the present invention, the data quality assurance device depicted in FIG. 6A can save to its database the first and last name of the patient to be treated, which is part of the "Plan Data" shown in FIG. 5. In clinics which use an automated patient-identification system (not depicted), such as a barcoded bracelet worn on the patient's wrist, or similar RFID identifying system, the patient's barcode or RFID would be scanned or "read" at the time that the patient enters the radiotherapy treatment room. By providing this identity data to the data quality assurance device depicted in FIG. 6A, it could display an alert, as in FIG. 6B, if the name of the patient, as physically scanned via barcode or RFID, did not match the name of the patient, as downloaded, thus alerting operators to the fact that they have downloaded the wrong patient's data, before they turn the beam on. (Medical errors of this type, in which a patient is wrongly treated using the radiation beams intended for another patient, constitute approximately 10% of the medical errors reported by New York State radiation therapy facilities—source: New York State Dept. of Health, Notice No. BERP 2004-1)

While the invention has been described herein with reference to specific embodiments, features and aspects, it will be recognized that the invention is not thus limited, but rather extends in utility to other modifications, variations, applications, and embodiments, and accordingly all such other modifications, variations, applications, and embodiments are to be regarded as being within the spirit and scope of the invention.

What is claimed is:

1. A method for providing real-time packet-level quality assurance of digitized data that controls an electromechanical device that are transmitted through a network between a transmitting computer and at least one terminal computer, comprising:

passively monitoring all data packets transmitted through the network between the transmitting computer and the at least one terminal computer;

selectively recording data packets that contain digitized data that controls an electromechanical device of a predetermined format to a database, wherein a data quality assurance device is arranged and constructed for passively monitoring, selectively recording, analyzing data packets transmitted through the network between the transmitting computer and the at least one terminal computer, and providing real-time display of the analysis results and at least one packet-copying device is arranged and constructed to copy all data packets transmitted between the transmitting computer and the at least one terminal computer to the data quality assurance device;

analyzing the data packets stored in the database by comparing a current set of digitized data recorded for a current session to a set of digitized data recorded during a previous session to detect differences between the digitized data recorded during the current session and the digitized data recorded during the previous session; and providing real-time output and display of analysis results.

2. The method of claim 1, wherein the transmitting computer is a central medical database server that stores medical and clinical information used by a medical institute, wherein the electromechanical device is radiation treatment equipment, and wherein the digitized data that controls the electromechanical device is radiation treatment data.

3. The method of claim 2, wherein the digitized data that controls the electromechanical device comprises multi-leaf collimator (MLC) data.

4. The method of claim 3, wherein the digitized data that controls the electromechanical device is selected from the group consisting of MLC configuration data for static radiation treatment and MLC configuration data for intensity modulated radiation therapy (IMRT).

5. The method of claim 2, wherein the digitized data comprises monitor unit (MU) data.

6. The method of claim 1, wherein additional packet-copying devices are arranged and constructed to copy all data packets transmitted between the transmitting computer and other of the plurality of terminal computers to the data quality assurance device.

7. The method of claim 1, wherein the at least one packet-copying device is selected from the group consisting of hubs, network taps, and mixtures thereof.

8. The method of claim 1, further comprising providing patient identifying data from an automated patient-identification system to the data quality assurance device and comparing the patient identifying data to patient identifying data associated with the current set of digitized data, and outputting an alert when there is a mismatch, wherein the digitized data comprises patient identifying data which associate a set of electromechanical device control data with a specific patient.

9. The method of claim 1, wherein the digitized data comprises treatment plan data; wherein the transmitting computer is a central medical database server that stores medical and clinical information; wherein the electromechanical device controlled by the digitized data is selected from the group consisting of a medical linear accelerator, an automated prescription-filling system, a stereotactic radiosurgery device, a CT scanning device, radiation treatment equipment and a X-ray device, and wherein the digitized data that controls the electromechanical device are patient treatment data.

10. The method of claim 9, wherein the digitized data recorded during the previous session are a previous treatment session and the digitized data recorded for the current session is a current treatment session.

11. The method of claim 10, wherein the digitized data for each treatment session for a given patient is identical.

12. The method of claim 10, wherein providing real-time output and display of analysis results comprises displaying differences between the digitized data for the current session and the digitized data for the previous session.

13. The method of claim 1, wherein analyzing the data packets stored in the database further comprises determining whether a current set of digitized data that controls the electromechanical device transmitted through the network between the transmitting computer and the at least one terminal computer for a current session would lead to a harmful or undesirable outcome by the electromechanical device being controlled.

14. A system comprising:
a transmitting computer;
at least one terminal computer connected to the transmitting computer by a network, wherein data packets are transmitted between the transmitting computer and the at least one terminal computer through the network;
a data quality assurance device connected to the network, wherein the data quality assurance device is arranged and constructed for: (1) passively monitoring all data packets transmitted between the transmitting computer and the at least one terminal computer; (2) selectively recording data packets that contain digitized data that controls an electromechanical device of a pre-determined format to a database; (3) analyzing the data packets stored in the by comparing a current set of digitized data recorded for a current session to a set of digitized data recorded during a previous session to detect a difference between the digitized data recorded during the current session and the digitized data recorded during the previous session and (4) providing real-time output and display of analysis results, wherein the network is a switched network comprising a switch for connecting the transmitting computer with a plurality of terminal computers, the plurality of terminal computers including the at least one terminal computer; and
at least one packet-copying device arranged and constructed to copy all data packets transmitted between the transmitting computer and the at least one terminal computer to the data quality assurance device.

15. The system of claim 14, wherein the transmitting computer is a central medical database server that stores medical and clinical information used by a medical institute, wherein the electromechanical device is controlled by the digitized data is radiation treatment equipment, and wherein the digitized data that controls the electromechanical device is radiation treatment data.

16. The system of claim 15, wherein the digitized data that controls the electromechanical device comprises multi-leaf collimator (MLC) data.

17. The system of claim 16, wherein the digitized data that controls the electromechanical device is selected from the group consisting of MLC configuration data for static radiation treatment and MLC configuration data for intensity modulated radiation therapy (IMRT).

18. The system of claim 14, wherein the at least one packet-copying device is selected from the group consisting of hubs, network taps, and mixtures thereof.

19. The system of claim 15, wherein the digitized data comprises monitor unit (MU) data.

20. The system of claim 14, wherein the digitized data comprises patient identifying data which associate a set electromechanical device control data with a specific patient.

21. The system of claim 14, wherein the transmitting computer is a central medical database server that stores medical and clinical information, wherein the electromechanical device is selected from the group consisting of a medical linear accelerator, an automated prescription-filling system, a stereotactic radiosurgery device, a CT scanning device, radiation treatment equipment and a X-ray device, and wherein the digitized data that controls the electromechanical device is patient treatment data.

* * * * *